(12) United States Patent
Duffy et al.

(10) Patent No.: US 11,622,855 B2
(45) Date of Patent: *Apr. 11, 2023

(54) PROSTHETIC MITRAL VALVE AND DELIVERY METHOD

(71) Applicant: Medtronic Vascular Galway, Galway (IE)

(72) Inventors: Niall Duffy, Galway (IE); Gavin Kenny, Galway (IE); Fabio Bartolozzi, Galway (IE)

(73) Assignee: MEDTRONIC VASCULAR GALWAY, Galway (IE)

( * ) Notice: Subject to any disclaimer, the term of this patent is extended or adjusted under 35 U.S.C. 154(b) by 263 days.

This patent is subject to a terminal disclaimer.

(21) Appl. No.: 16/747,900

(22) Filed: Jan. 21, 2020

(65) Prior Publication Data
US 2020/0214837 A1 Jul. 9, 2020

Related U.S. Application Data

(60) Continuation of application No. 15/657,520, filed on Jul. 24, 2017, now Pat. No. 10,537,429, which is a
(Continued)

(51) Int. Cl.
*A61F 2/24* (2006.01)
*A61B 17/04* (2006.01)

(52) U.S. Cl.
CPC ........ *A61F 2/2427* (2013.01); *A61B 17/0401* (2013.01); *A61F 2/2412* (2013.01);
(Continued)

(58) Field of Classification Search
CPC .... A61F 2/2427; A61F 2/2412; A61F 2/2454; A61F 2/2457; A61B 17/0401
See application file for complete search history.

(56) References Cited

U.S. PATENT DOCUMENTS 4,960,424 A 10/1990 Grooters
5,662,704 A 9/1997 Gross
(Continued)

FOREIGN PATENT DOCUMENTS

WO 2009/033469 A1 3/2009
WO 2011/072084 A2 6/2011
(Continued)

OTHER PUBLICATIONS

PCT Search Report & Written Opinion dated Feb. 5, 2014, in International Application No. PCT/US2013/063938.

*Primary Examiner* — Tuan V Nguyen
(74) *Attorney, Agent, or Firm* — Medler Ferro Woodhouse & Mills PLLC

(57) ABSTRACT

A valve prosthesis and methods for implanting the prosthesis are provided. The prosthesis generally includes a self-expanding frame and two or more engagement arms. A valve prosthesis is sutured to the self-expanding frame. Each engagement arm corresponds to a native mitral valve leaflet. At least one engagement arm immobilizes the native leaflets, and holds the native leaflets close to the main frame. The prosthetic mitral valve frame also includes two or more
(Continued)

anchor attachment points. Each anchor attachment point is attached to one or more anchors that help attach the valve prosthesis to the heart.

18 Claims, 10 Drawing Sheets

Related U.S. Application Data continuation of application No. 14/676,926, filed on Apr. 2, 2015, now Pat. No. 9,744,036, which is a division of application No. 13/664,652, filed on Oct. 31, 2012, now Pat. No. 9,023,099.

(52) U.S. Cl.
CPC .......... *A61F 2/2418* (2013.01); *A61F 2/2454* (2013.01); *A61F 2/2457* (2013.01); *A61B 2017/044* (2013.01); *A61B 2017/0409* (2013.01); *A61B 2017/0414* (2013.01); *A61B 2017/0417* (2013.01); *A61B 2017/0464* (2013.01); *A61F 2210/0057* (2013.01); *A61F 2220/0016* (2013.01); *A61F 2220/0041* (2013.01); *A61F 2220/0075* (2013.01); *A61F 2230/005* (2013.01); *A61F 2230/008* (2013.01); *A61F 2230/0013* (2013.01); *A61F 2250/0004* (2013.01); *A61F 2250/0012* (2013.01); *A61F 2250/0039* (2013.01)

(56) References Cited

U.S. PATENT DOCUMENTS

| | | |
|---|---|---|
| 6,332,893 B1 | 12/2001 | Mortier et al. |
| 6,830,586 B2 | 12/2004 | Quijano et al. |
| 7,591,847 B2 | 9/2009 | Navia et al. |
| 8,043,368 B2 | 10/2011 | Crabtree |
| 9,023,099 B2 | 5/2015 | Duffy |
| 2001/0050020 A1 | 12/2001 | Davis et al. |
| 2008/0071368 A1 | 3/2008 | Tuval et al. |
| 2008/0125860 A1 | 5/2008 | Webler et al. |
| 2010/0161041 A1* | 6/2010 | Maisano ............... A61F 2/2427 128/898 |
| 2011/0004296 A1* | 1/2011 | Lutter .................. A61F 2/2487 623/1.26 |
| 2011/0106245 A1 | 5/2011 | Miller et al. |
| 2011/0112632 A1 | 5/2011 | Chau et al. |
| 2011/0137397 A1 | 6/2011 | Chau et al. |
| 2011/0208297 A1 | 8/2011 | Tuval et al. |
| 2011/0208298 A1* | 8/2011 | Tuval ................... A61F 2/2418 623/2.17 |
| 2011/0224785 A1 | 9/2011 | Hacohen |
| 2011/0264206 A1 | 10/2011 | Tabor |

FOREIGN PATENT DOCUMENTS

| | | |
|---|---|---|
| WO | 2011/137531 A1 | 11/2011 |
| WO | 2012/004679 A2 | 1/2012 |

\* cited by examiner

PROSTHETIC MITRAL VALVE AND DELIVERY METHOD

CROSS-REFERENCE TO RELATED APPLICATIONS

This application is a continuation of prior U.S. application Ser. No. 15/657,520, filed Jul. 24, 2017, now U.S. Pat. No. 10,537,429, which is a continuation of U.S. application Ser. No. 14/676,926, filed Apr. 2, 2015, now U.S. Pat. No. 9,744,036, which is a divisional of U.S. application No. 13/664,652, filed Oct. 31, 2012, now U.S. Pat. No. 9,023,099, the contents of which are incorporated by reference herein in their entirety.

BACKGROUND OF THE INVENTION

Field of the Invention

The present invention is related to artificial heart valves. More specifically, the present invention is directed to artificial mitral valve prostheses and method of implanting the prostheses leading to reduction of myocardial wall tension and the repair of mitral valve insufficiency.

Background

The mitral valve is a functional organ composed of multiple dynamically interrelated units. During cardiac cycle, the fibrous skeleton, the anterior and posterior leaflets, the papillary muscles, the *chordae tendinea*, and the ventricular and atrial walls all interplay to render a competent valve. The complex interaction between the mitral valve and the ventricle by the subvalvular apparatus (the papillary muscles and the *chordae tendinea*) is essential in maintaining the continuity between the atrio-ventricular ring (which is part of the fibrous skeleton of the heart) and the ventricular muscle mass, which provides for the normal functioning of the mitral valve.

Like all heart valves, the mitral valve exhibits two types of pathologies: regurgitation (i.e., abnormal leaking of blood from the left ventricle, through the mitral valve, and into the left atrium, when the left ventricle contracts) and stenosis (i.e., narrowing of the orifice of the mitral valve of the heart). Regurgitation is the more common of the two defects. Typically, either defect can be treated by surgical repair. However, surgical repair is not always feasible since many patients requiring mitral valve replacement are inoperable or deemed to pose too high a surgical risk because of extensive fibrosis, leaflets calcification, or massive *chordae* rupture. Further, such surgical procedures are traumatic. Additionally, surgical procedures can lead to an interruption of the mitral annulus-papillary muscle continuity, which accounts for changes in geometry mechanics and performance of the left ventricle. These problems are lessened by the emerging techniques for minimally invasive mitral valve repair, but still many of those techniques require arresting the heart and funneling the blood through a heart-lung machine, which can also be traumatic for patients.

In certain cases, the mitral valve cannot be repaired and must be replaced. Valve replacement can create additional problems including limitation of the mitral flow during exercise due to a small effective orifice area and high cardiac output imposed by a smaller size artificial valve as compared with the natural valve orifice area. Further, the rigid structure of an artificial valve prevents the physiologic contraction of the posterior wall of the left ventricle surrounding the mitral annulus during systole. Also, myocardial rupture can result from excision or stretching of the papillary muscle in a thin and fragile left ventricle. Additionally, *chordae* rupture can also occur due to the *chordae* rubbing against the artificial valve over time, leading to increased heart wall stress. It has been shown that severing the *chordae* can lead to a 30% reduction in chamber function. Thus, mitral valve replacement has a high mortality rate in very sick, chronic heart failure patients.

The *chordae tendinea*, which connect the valve leaflets to the papillary muscles (PM) act like "tie rods" in an engineering sense. Not only do the *chordae* tendinea prevent prolapse of the mitral valve leaflets during systole, but they also support the left ventricular muscle mass throughout the cardiac cycle. To function adequately, the mitral valve opens to a large orifice area and, for closure, the mitral leaflets have an excess surface area (i.e. more than needed to effectively close the mitral orifice). On the other hand, systolic contraction of the posterior ventricular wall around the mitral annulus (MA) creates a mobile D-shaped structure with sphincter-like function which reduces its area by approximately 25% during systole, thus exposing less of the mitral leaflets to the stress of the left ventricular pressure and flow.

It has been long postulated that the structural integrity of the MA-PM continuity is essential for normal left ventricular function. Recent evidence supports the concept that preservation of the subvalvular apparatus with the MA-PM continuity in any procedure on the mitral valve is important for the improved long-term quality and quantity of life following valve replacement. Maintaining the MA-PM continuity, thus, appears to provide a substantial degree of protection from the complications associated with valve replacement.

Therefore, what is needed is a mitral valve prosthesis and method of implantation that minimizes the traumatic impact on the heart while effectively replacing native leaflet function. A consistent, reproducible, and safe method to introduce a prosthesis into the mitral position in a minimally invasive fashion could be attractive for numerous reasons: a) it can treat both functional and degenerative mitral regurgitation (MR); b) it can treat mitral stenosis; c) it can offer a remedy to inoperable patients, high risk surgical patients, and those that cannot tolerate bypass; d) it can allow a broad range of practitioners to perform mitral valve procedures; and/or e) it can enable more consistency in measuring outcome.

BRIEF SUMMARY OF THE INVENTION

Provided herein are mitral valve prostheses and methods for implanting the prostheses in the heart. The prostheses generally include a self-expanding frame and two or more engagement arms. A valve prosthesis is sutured to the self-expanding frame. Each engagement arm corresponds to a native mitral valve leaflet. At least one engagement arm immobilizes the native leaflets, and holds the native leaflets close to the main frame. Such configuration achieves numerous goals. For example, such configuration achieves one or more of the following: prevents the native leaflets from obstructing flow through the left ventricular outflow tract (LVOT); prevents the native leaflets from interacting with the prosthetic leaflets; recruits the native leaflets in minimizing peri-valvular leaks; maintains proper alignment of the valve prosthesis; avoid systolic anterior mobility; and maintains valve stability by preventing migration of the valve into the atrium or ventricle and prevents damage to the native *chordae*. Additionally, the prosthetic mitral valve frame can include two or more anchor attachment points. Each anchor attachment point can be attached to one or more anchors that help attach the mitral valve to the heart. Such configuration provides added stability to the prosthetic mitral valve and prevents damage to the native *chordae*. The design of the prosthesis also mimics the native valve and supports a non-circular in vivo configuration, which better reflects native valve function.

In certain embodiments, the mitral valve prosthesis comprises an expandable inflow region formed of a plurality of cells, an expandable outflow region formed of a plurality of cells, and a prosthetic valve. The expandable inflow region has a cross-sectional diameter larger than the annulus of the native mitral valve and can be configured to expand within and support against the walls of the left atrium. The expandable outflow region can be configured to expand within and support against the native mitral valve annulus and comprises two or more engagement arms and at least two anchor attachment points.

In certain embodiments, a mitral valve disorder in a patient's heart can be treated by a method comprising the steps of: (a) inserting a delivery device into the left ventricle of the heart, (b) advancing a mitral valve prosthesis via the delivery device into the left ventricle of the heart, (c) advancing the delivery device into the native mitral valve such that the engagement arms seat on the outer surface of the native mitral valve leaflets, (d) attaching the mitral valve prosthesis to the heart via at least one anchor, and (e) adjusting tension on the anchor to prevent peri-valvular leakage.

BRIEF DESCRIPTION OF THE DRAWINGS/FIGURES

The accompanying figures, which are incorporated herein, form part of the specification and illustrate embodiments of a mitral valve prosthesis and methods of implantation. Together with the description, the figures further serve to explain the principles of and to enable a person skilled in the relevant art(s) to make, use, and implant the valve prosthesis described herein. In the drawings, like reference numbers indicate identical or functionally similar elements.

DETAILED DESCRIPTION OF THE INVENTION

The following detailed description of mitral valve prostheses and methods for implantation refers to the accompanying figures that illustrate exemplary embodiments. Other embodiments are possible. Modifications can be made to the embodiments described herein without departing from the spirit and scope of the present invention. Therefore, the following detailed description is not meant to be limiting.

Figure 1:
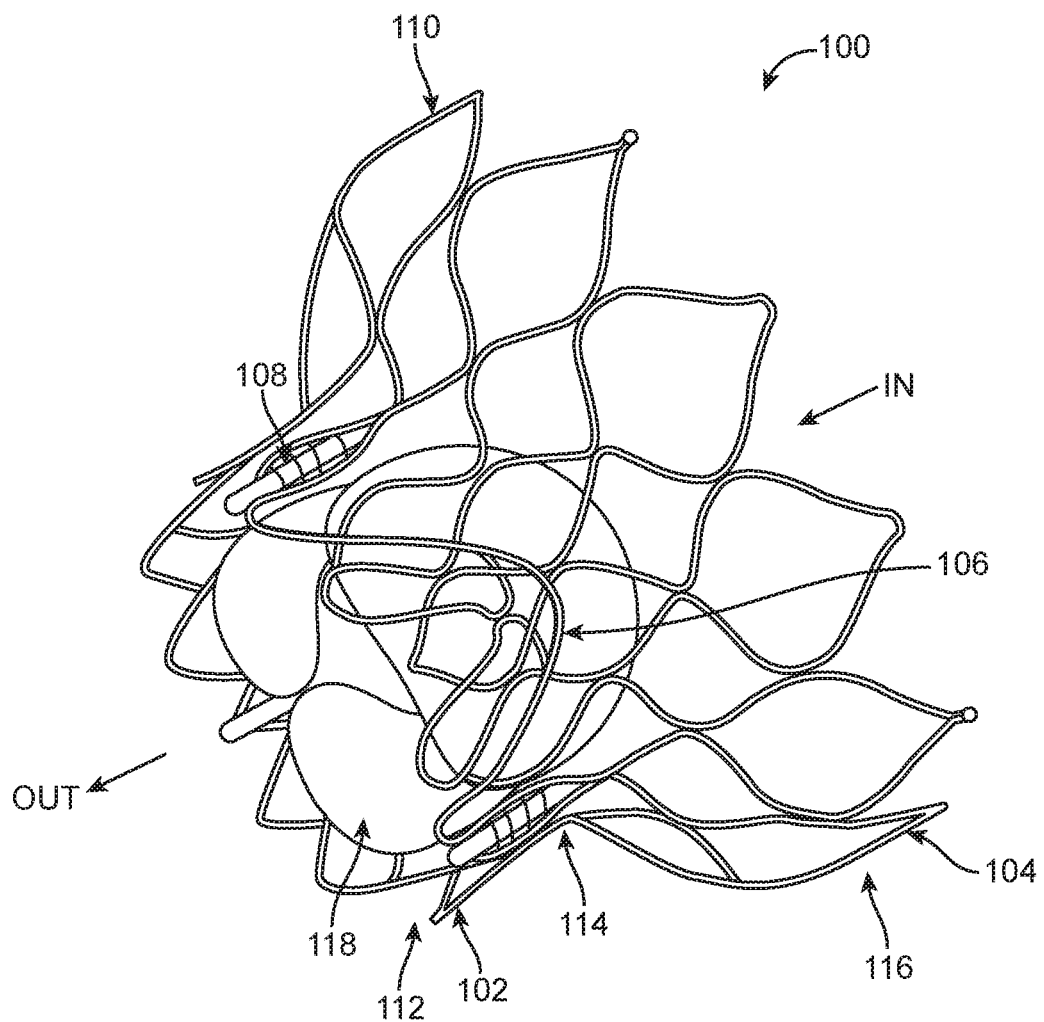
FIG. 1 is a perspective view of a mitral valve prosthesis, according to an aspect of this disclosure.

FIG. 1 is a perspective view of a mitral valve prosthesis 100, in accordance with one embodiment presented herein. Prosthesis 100 comprises a non-cylindrical inner support structure 102 located at the outflow end of mitral valve prosthesis 100. Non-cylindrical shapes can be used to improve the anchoring and/or orientation of the prosthetic valve at the desired implantation site. In addition, inner support structure 102 can have one or more sections configured to expand to a restricted or preset diameter rather than to expand until restrained by surrounding anatomical structures. Control of the expansion diameter provides a portion of inner support structure 102 with a predetermined configuration irrespective of the surrounding anatomy. The valve geometry in the expanded configuration can be enhanced in prostheses with controlled expansion diameters.

In one aspect of the invention, inner support structure 102 can comprise a generally axially-curved configuration or a concave configuration. Such configurations can further resist deviations from the optimal valve support expansion configuration. This is because variations in the mechanical stress exerted from the inflow zone of proximal section 116 and/or outflow zone of distal section 112, caused by anatomical and pathological variations of surrounding structures, will be dispersed along the entire length of prosthesis 100. As used herein the term "distal" is understood to mean downstream to the direction of blood flow. The term "proximal" is intended to mean upstream to the direction of blood flow. As a result, any detrimental effects to prevent expansion of valve prosthesis 100 to its optimal expansion configuration are minimized and prevented. In comparison, a prosthesis frame with a more cylindrical shape responds less predictably to variations in a patient's anatomy and can kink and/or bow after implantation. Such kinking and or bowing disrupts the geometry of the valve that is resistant to expansion variations of adjacent zones. By providing a consistent expanded configuration for the valve prosthesis 100 that is resistant to expansion changes of adjacent zones, a consistent valve geometry is achieved and valve function can be improved.

Mitral valve prosthesis 100 also includes an outer support structure 104 located at the inflow end of mitral valve prosthesis 100. As shown, mitral valve prosthesis 100 includes two engagement arms 106 attached to inner support structure 102 to anatomically match the native mitral valve leaflets (not shown). Upon implantation outer engagement arms 106 clamp and immobilize the native mitral valve leaflets, and hold the native leaflets close to outer support structure 104. Each outer engagement arm 106 includes a trough and an upward concave structure having ends meeting at commissure post 108. In one aspect of the invention, the inner support structure 102 comprises two commissure posts 108, wherein ends of the engagement arms are each coupled to one of the commissure posts. In another embodiment, the inner support structure 102 further comprises more than two commissure posts 108, wherein ends of the engagement arms are each coupled to one of the commissure posts. Inner support structure 102 further includes an opening to facilitate attaching outer support structure 104 to inner support structure 102. In a further aspect of the invention, inner support structure 102 includes commissural sealing members (not shown) to provide an effective seal between the outer support structure 104 of the mitral valve prosthesis 100 and the walls of the atrium (not shown), thereby sealing the native commissures of the heart and preventing peri-valvular leakage.

Inner support structure 102 includes a generally uniform, circular cross-section along the length of the longitudinal axis of valve prosthesis 100. In an alternative embodiment, proximal section 116 can also include fixation barbs to provide further fixation and to prevent migration of prosthesis 100 into the ventricle. As shown, distal section 112, narrow throat section 114, and proximal section 116 include diamond-shaped cells 110. Alternative shapes and configurations of the cells (or struts) 110 can be employed. The diamond-shaped cells 110 are generally equal in size. However, each column of cells can have different sizes. Alternatively, cells located near the distal section 112 of prosthesis 100 can be smaller than cells located near proximal section 116.

Any suitable combination of these embodiments can also be used. For example, for each cell, the location of the junction of members between adjacent cells can be positioned asymmetrically. Inner support structure 102 can comprise curvilinear structural members to form asymmetrical cells. In an alternative embodiment, inner support structure 102 can comprise structural members formed in a generally zig-zag configuration to form symmetrical or asymmetrical cells. The zig-zag configuration is believed to improve upon otherwise straight members, by distributing the stress associated with radial expansion and contraction to a plurality of points between junctions. As with the above embodiments, inner support structure 102 can be configured with heterogeneous patterns of cells or homogeneous patterns of cells, or both.

Individual cells of a prosthesis frame can be characterized by their relative length and width. It is generally preferred that the ratio of the cell length to width be about 0.5 to about 3.0, more preferably about 1.5 to 2.5 and most preferably about 1.75 to about 2.25. Cell configurations having size ratios generally within these ranges are believed to have improved expansion and structural characteristics.

Distal section 112 can be formed in a straight fashion (i.e., cylindrical and parallel to the longitudinal axis of prosthesis 100) or in a flared fashion (i.e., diverging away from the longitudinal axis of prosthesis 100). Proximal section 116 is generally formed to bulge outward from narrow throat section 114, and can be formed straight or flared outward. Proximal section 116 is the blood inlet end of valve prosthesis 100. In one aspect of the disclosure, proximal section 116 is wider than narrow throat section 114, and is wider than the native valve segment at the native valve annulus. Such a configuration prevents migration of prosthesis 100 into the ventricle and improves sealing of prosthesis 100 against the atrial wall.

Inner support structure 102 is also configured to be expandable (preferably self-expandable), and can be formed of a memory alloy such as NITINOL. Other biocompatible metals can also be used. Outer support structure 104 can also be formed of a memory alloy such as NITINOL, or other biocompatible metals. Inner support structure 102 and outer support structure 104 can be integrally formed, or can comprise separate modular components that are attached to one another. In one embodiment, inner support structure 102 is designed to flex and deform so as to mimic the natural cardiac movements of the heart through the cardiac cycle. In another embodiment, inner support structure 102 is designed in a rigid fashion to avoid flexing or deformation during the cardiac cycle.

A prosthetic valve 118 can be attached to inner support structure 102. In one embodiment, valve 118 is sewn onto inner support structure 102 as described in U.S. Patent Application Publication No. 2008/0071368, which is incorporated herein by reference in its entirety. In one aspect of the disclosure, valve 118 can be formed of a biocompatible synthetic material, synthetic polymer, an autograft tissue, xenograft tissue, or other alternative materials. In a further aspect of the invention, valve 118 can be a tri-leaflet bovine pericardium valve, a bi-leaflet valve, or any other suitable valve.

Alternative designs can include three engagement arms, three leaflets, three anchor attachment points, and/or three commissure posts.

Figure 2:
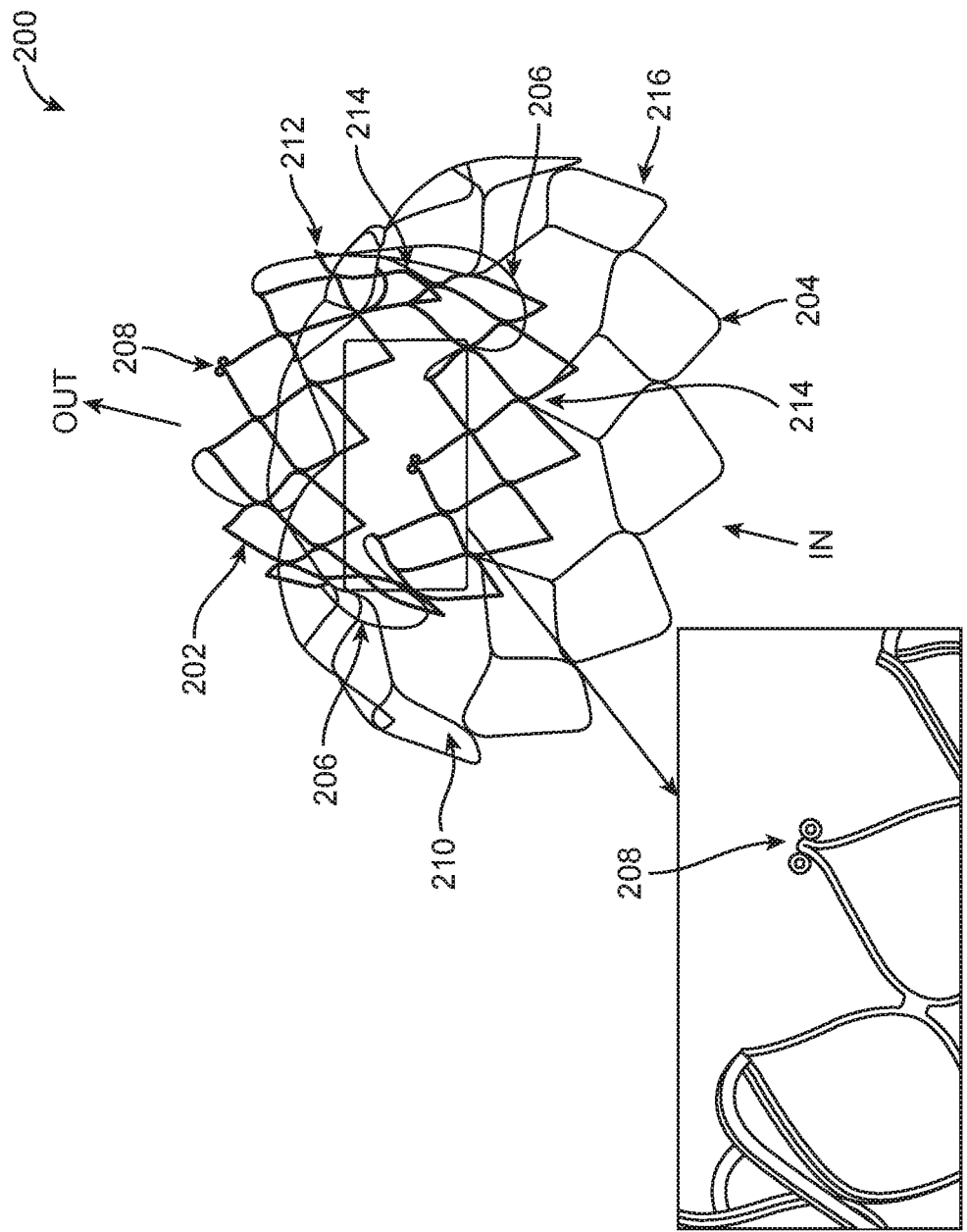
FIG. 2 is a perspective view of a frame of a mitral valve prosthesis and a close-up view of the frame showing the anchor attachment points, according to an aspect of this disclosure.

FIG. 2 is a perspective view of a frame of a mitral valve prosthesis 200, in accordance with an alternative aspect of the invention. Similar to mitral valve prosthesis 100 of FIG. 1, mitral valve prosthesis 200 includes an outer support structure 204 and an inner support structure 202, which includes a distal section 212, a relatively narrow throat section 214, and a proximal section 216. Inner support structure 202 includes outer engagement arms 206. As shown, distal section 212, narrow throat section 214, and proximal section 216 include diamond-shaped cells 210. Alternative shapes and configurations of the cells (or struts) can be employed. Mitral valve prosthesis 200 includes all the features of prosthesis 100 and further includes anchor attachment points 208 on inner support structure 202. The anchor attachment points 208 can attach to the heart via one or more anchors to provide further fixation support and to prevent migration of prosthesis 200 into the ventricle. The anchors disclosed herein are very robust and greatly improve the stability of mitral valve prosthesis 200 which lessens the possibility of migration due to *chordae* rupture. The anchors take the strain off of the native *chordae* and help reduce the tendency for them to break over time. In addition, the anchors can be tensioned to help prevent and/or stop peri-valvular leakage.

Like prosthesis 100, a prosthetic valve (not shown) can be attached to inner support structure 202. In one aspect of the invention, the prosthetic valve is sewn onto inner support structure 202, as described in U.S. Patent Application Publication No. 2008/0071368, which is incorporated herein by reference in its entirety. The prosthetic valve can be formed of a biocompatible synthetic material, synthetic polymer, an autograft tissue, xenograft tissue, or other alternative materials. In a further aspect of the invention, inner support structure 202 includes commissural sealing members (not shown) to provide an effective seal between the outer support structure 204 of the mitral valve prosthesis 200 and the walls of the atrium (not shown), thereby sealing the native commissures of the heart and preventing peri-valvular leakage.

Referring now to FIGS. 3A-3F, a method of implanting a mitral valve prosthesis 302 will now be described. Mitral valve prosthesis 302 includes all the features of valve prostheses 100 and 200. In one aspect of the invention, delivery device 340 is inserted through mitral annulus 317 into the left ventricle and mitral valve prosthesis 302 can be deployed into mitral annulus 317. As shown, papillary muscle 316 and *chordae* 314 are positioned in the left ventricle. *Chordae* 314 connect native valve leaflets (not shown) to papillary muscle 316. Delivery device 340 includes a deployment element 360 having a distal tip 308. Deployment element 360 is advanced into the left ventricle such that the engagement arms 306 of the mitral valve prosthesis 302 seat on the outer surface of the native mitral valve leaflets at the mitral annulus 317. Delivery device 340 can be rotated and adjusted as necessary to align the valve prosthesis so that engagement arms 306 are positioned to clamp the native valve leaflets. Proper seating of the mitral valve prosthesis 302 at the mitral annulus 317 is achieved by the engagement arms 306 capturing the native mitral valve leaflets. The radial force generated by the mitral valve prosthesis 302 in the atrium against engagement arms 306 creates a "sandwich effect" by pinching the native mitral valve leaflets and atrial tissue against the inner support structure of mitral valve prosthesis 302.

In a further aspect of the invention, the user can control the speed of deployment of valve prosthesis 302 by modifying the rate at which the user pushes deployment element 360 in the distal direction. In certain instances, the user may wish to reposition the prosthetic valve after beginning to deploy the prosthetic valve. The user can accomplish this by moving the entire delivery device 340 in a distal or proximal direction. In certain embodiments, delivery device 340 and deployment element 360 can be generally cylindrical in shape.

In one aspect of the invention, delivery device 340 is a trocar. In another aspect of the invention, the delivery device 340 is a catheter. In certain embodiments, parts of delivery device can be made from biocompatible materials, such as certain biocompatible polymers and biocompatible metals known in the art.

In a further aspect of the invention, deployment element 360 is attached to anchor attachment points 312 of mitral valve prosthesis 302 via anchors 310. In one aspect of the invention, anchors 310 are attached at a first end to attachment points 312 of mitral valve prosthesis 302 prior to delivery of mitral valve prosthesis 302. A second end of anchors 310 extend through distal tip 308 of deployment element 360 though delivery device 340 to the outside of the patient. In one aspect of the invention, anchors 310 are artificial *chordae*.

In one aspect of the invention, each anchor attachment point 312 includes a single eyelet. In another aspect of the invention, each anchor attachment point 312 includes at least two eyelets. In another aspect of the invention, each anchor attachment point 312 includes at least one hook. In another aspect of the invention, each anchor attachment point 312 includes at least one clip. In another aspect of the invention, each anchor attachment point 312 includes at least one screw. In another aspect of the invention, each anchor attachment point 312 includes at least two of any combinations of an eyelet, a hook, a clip and/or a screw.

In one aspect of the invention, anchor 310 is a suture comprised of a biocompatible material. In another aspect of the invention, anchor 310 is a wire comprised of a biocompatible material. In another aspect of the invention, anchor 310 is a chord comprised of a biocompatible material. In another aspect of the invention, the anchor is any biocompatible material. In one aspect, the biocompatible material is linearly elastic. In another aspect, the biocompatible material is viscoelastic. In yet another aspect, the biocompatible material can be engineered to have any desired property. In one embodiment, the biocompatible material can be a composite fiber of PTFE, elastane, and binder. In another embodiment, the biomaterial can also be an autograft, allograft, or xenograft used as a transplant material. In another embodiment, the biomaterial can be formed of a memory alloy such as NITINOL. In yet another embodiment, the biomaterial can be any biocompatible polymer or biocompatible metal known in the art. In one aspect, the elastic nature of the biocompatible material is optimized so it can provide a constant force and not elongate over time. In another aspect, the biocompatible material can be reinforced to have optimum fatigue performance. In one embodiment, the anchor is configured to function as a tether. In yet another embodiment, the anchor can be configured to function as an artificial *chordae*. In still another embodiment, the anchor can be configured to function as an anchoring element.

After deployment of mitral valve prosthesis 302, delivery device 340 and deployment element 360 are retracted while mitral valve prosthesis 302 remains attached to delivery device 340 and distal tip 308 of the deployment element 360 via anchors 310.

Figure 3A:
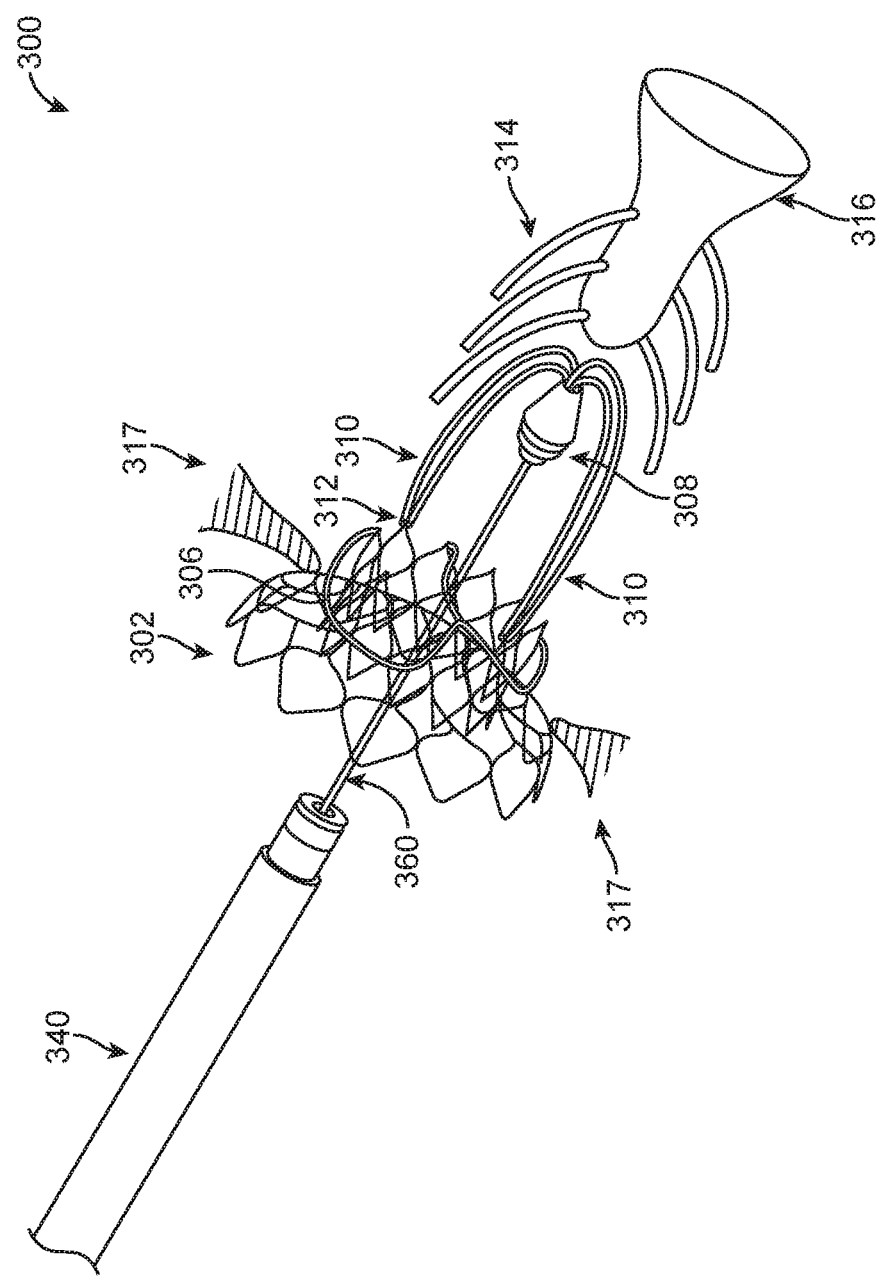
FIG. 3A is a schematic view of a valve prosthesis and delivery system according to an aspect of this disclosure.
Figure 3B:
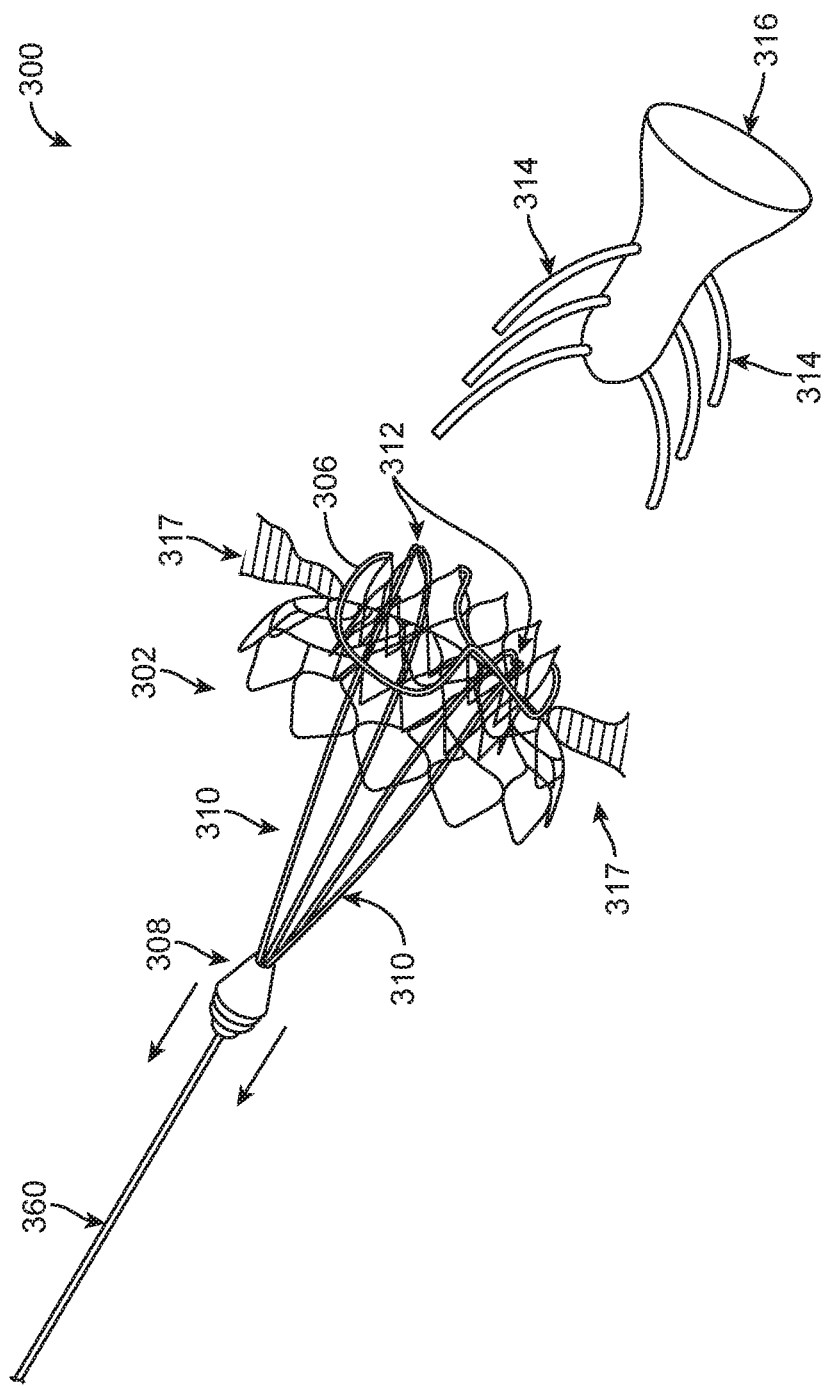
FIG. 3B is a schematic view of a valve prosthesis and delivery system according to an aspect of this disclosure.
Figure 3C:
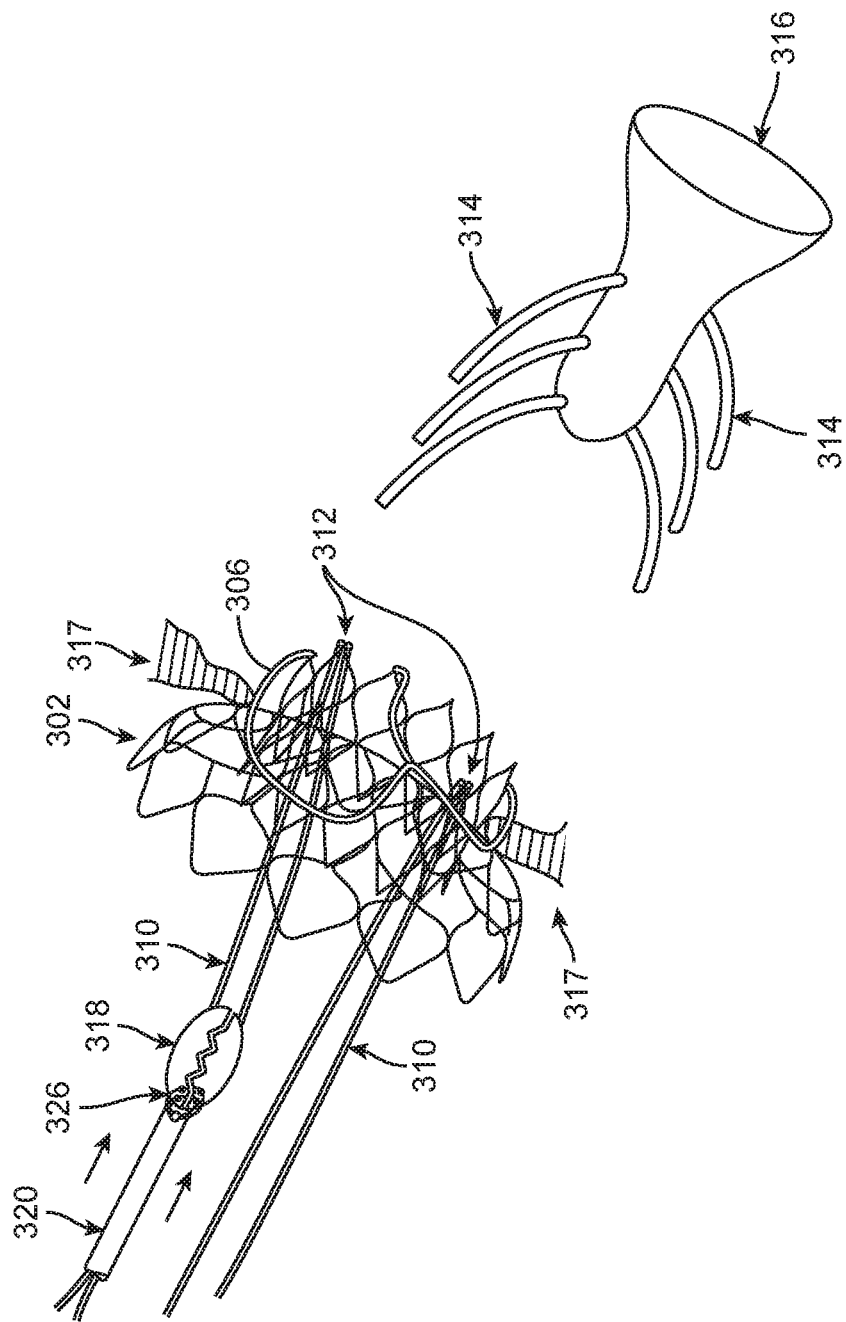
FIG. 3C is a schematic view of a valve prosthesis and delivery system according to an aspect of this disclosure.
Figure 3D:
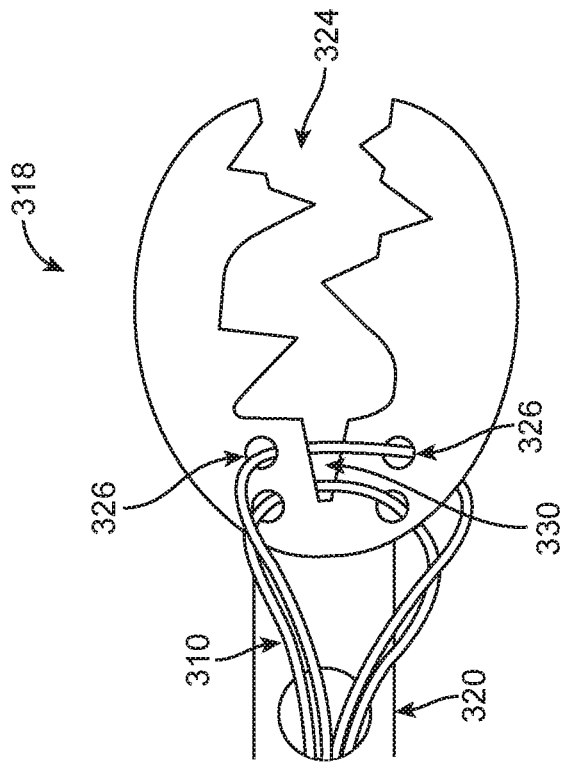
FIG. 3D is a schematic view of a valve prosthesis and delivery system according to an aspect of this disclosure.
Figure 3D:
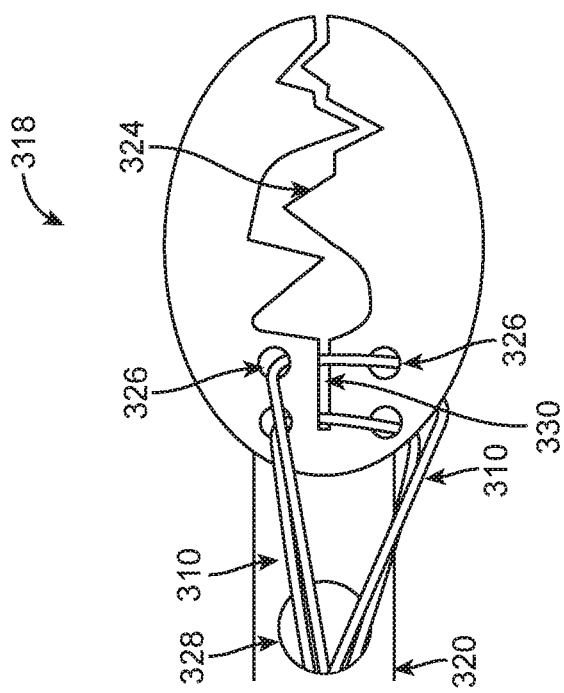

As shown in FIGS. 3C-3D, the second ends of anchors 310 are disengaged from the distal tip 308 of the deployment element 360 and passed through holes 326 of an anchoring element 318 into an anchoring element delivery device 320. In a further aspect of the invention, anchors 310 pass across lock 330 of anchoring element 318. In one aspect of the invention, anchoring element 318 is a clip and includes jaws 324. In alternative aspect of the invention, the anchoring element 318 can be a hook, screw, or other attachment known in the art. In one aspect of the invention, the anchoring element delivery device 320 is cylindrical in shape.

In one aspect of the invention, anchors 310 are woven through holes 326 in the anchoring element 318 and then passed into an anchoring element delivery device 320 through opening 328 in the anchoring element delivery device 320. The jaws 324 of the anchoring element 318 are provided to attach anchoring element 318 and anchors 310 to heart tissue. In one aspect of the invention, jaws 324 of the anchoring element 318 can attach to a papillary muscle 316 of the heart by gripping and holding onto papillary muscle 316 tissue within jaws 324. In one aspect of the invention, jaws 324 are configured to allow for proper tensioning of anchors 310. For example, when jaws 324 are open, anchors 310 can be tensioned through anchor element delivery device 320 by adjusting the length of anchors 310. When jaws 324 are closed, lock 330 on anchoring element 318 clamps anchors 310 such that the length of anchors 310 cannot be adjusted to adjust the tension. In one aspect, jaws 324 are closed onto heart tissue after proper tensioning of the anchors 310 is achieved. As disclosed herein, jaws 324 are open when tissue or other heart structure can be passed into jaws 324 into an interior area of anchoring element 318. Jaws 324 are opened to allow jaws 324 to attach to heart tissue and to allow for tensioning of anchors 310.

In another aspect of the invention, anchors 310 can be attached to papillary muscle 316 or other heart structure prior to implantation of mitral valve prosthesis 302. In this aspect, the practitioner would be able to check the securement of anchoring element 318 prior to commencing valve implantation.

Figure 3E:
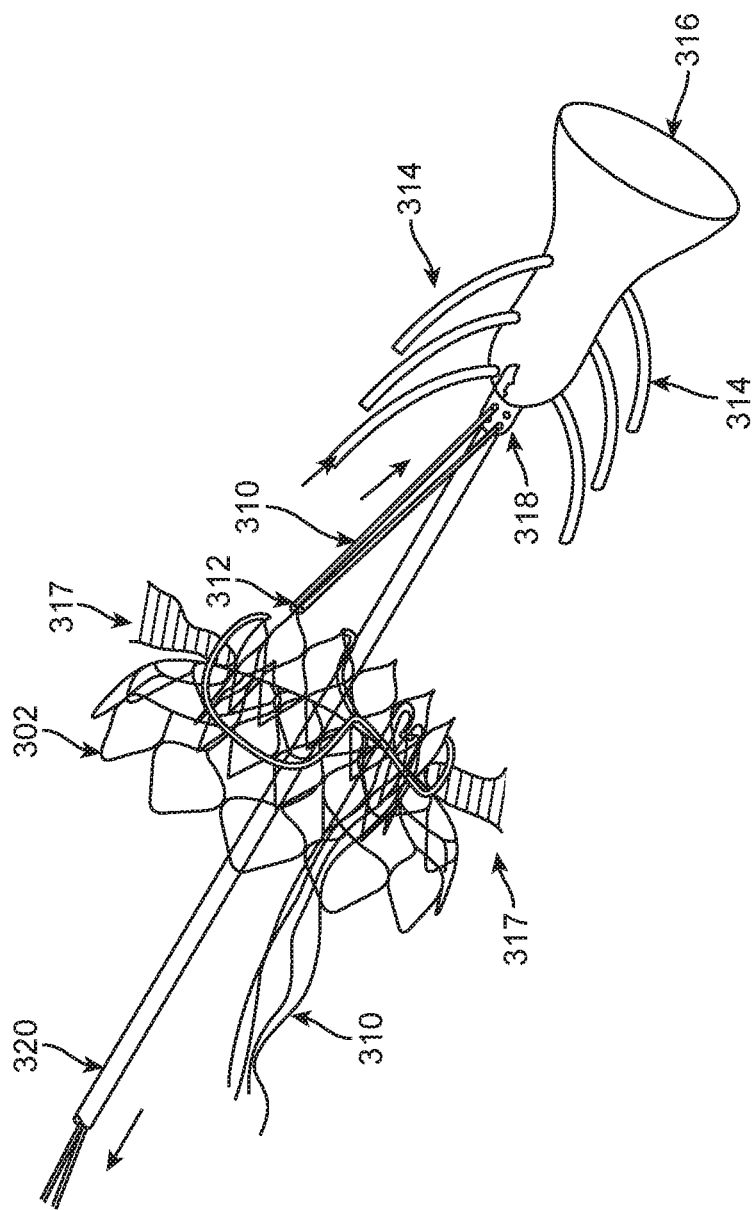
FIG. 3E is a schematic view of a valve prosthesis and delivery system according to an aspect of this disclosure.

As shown in FIG. 3E, the anchoring element 318 and anchors 310 are advanced into the left ventricle via the anchoring element delivery device 320 in order to attach to heart tissue or other structure in the left ventricle. In one embodiment, the anchoring element 318 is attached to a papillary muscle 316 of the heart. As a result, mitral valve prosthesis 302 is connected to the papillary muscle 316 of the heart though anchor attachment points 312, anchors 310, and anchoring element 318. In one embodiment, the anchoring element 318 is attached to second ends of the anchors 310.

Figure 3F:
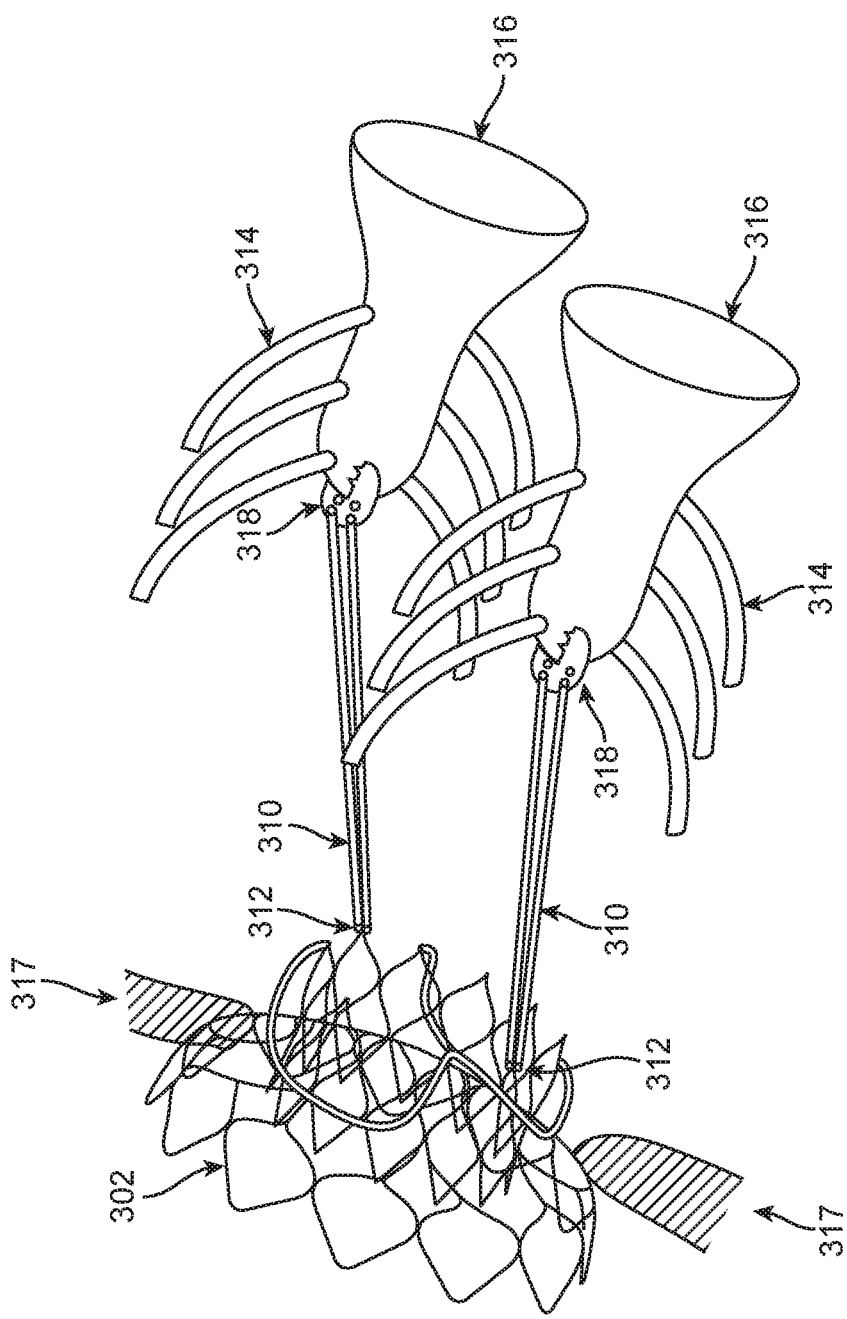
FIG. 3F is a schematic view of a valve prosthesis and delivery system according to an aspect of this disclosure.

FIG. 3F depicts a mitral valve prosthesis 302 properly positioned at the mitral annulus 317 and attached to the papillary muscles 316 of the heart via the anchors 310. Prior to closing jaws 324 on anchoring element 318, tension on the anchors 310 is adjusted as required in order to secure the mitral valve prosthesis 302 at the mitral annulus 317. In a further aspect of the invention, a practitioner can check for peri-valvular leakage (PVL) prior to completion of the valve replacement procedure. If leakage is present, anchors 310 can be tensioned to stop the leakage by opening jaws 324 on anchoring element 318 to release lock 330 to adjust the length of anchors 310 through anchoring element delivery device 320. After the practitioner verifies that no leakage is present around mitral valve prosthesis 302, anchoring element delivery device 320 is detached and withdrawn.

The anchors disclosed herein are very robust and greatly improve the stability of mitral valve prosthesis 200 which lessens the possibility of migration due to *chordae* fracture. The anchors take the strain off of the native *chordae* and help reduce the tendency for them to break over time. In addition, the anchors can be tensioned to add to the sandwich effect and help prevent and/or stop peri-valvular leakage.

Figure 4A:
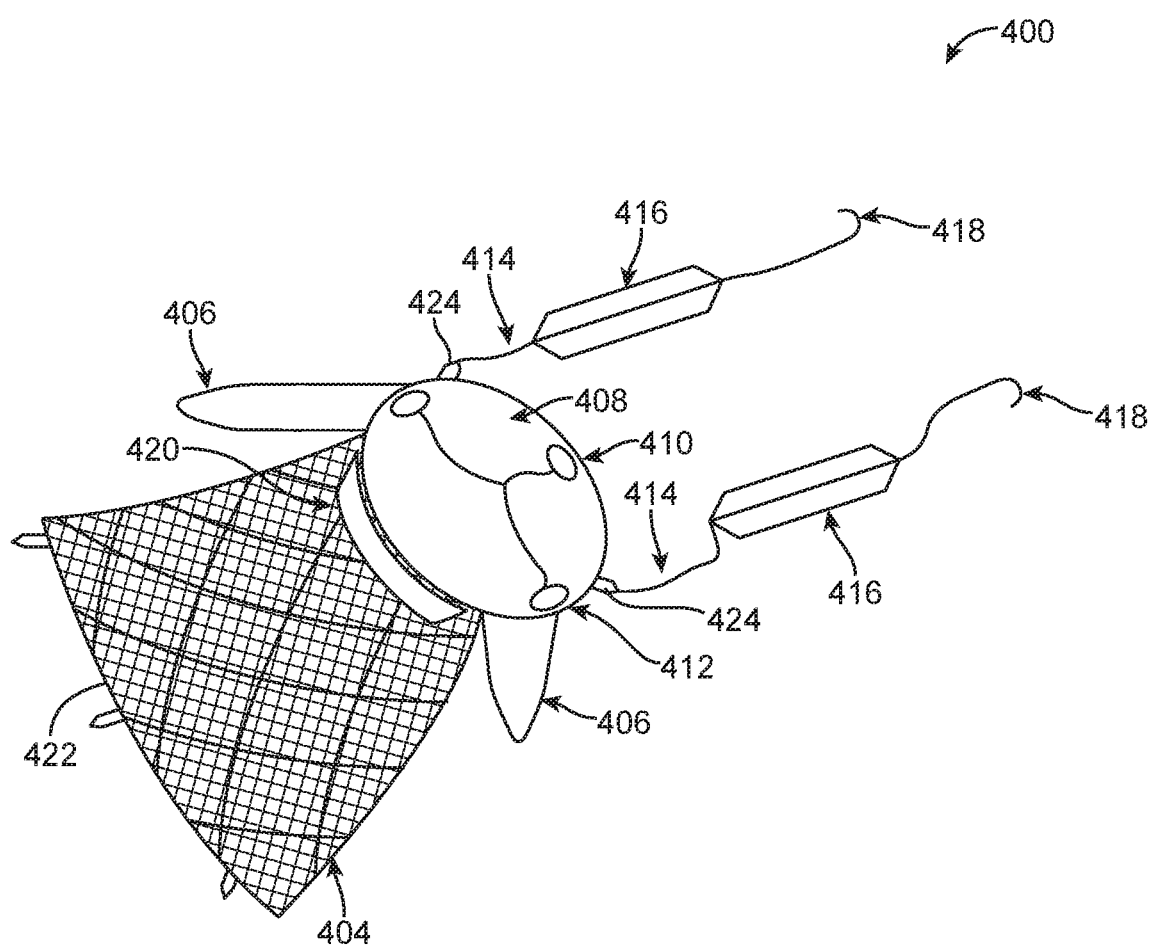
FIG. 4A is a perspective view of a mitral valve prosthesis, according to an aspect of this disclosure.

FIG. 4A is a perspective view of a mitral valve prosthesis 400, in accordance with an alternative aspect of the invention. Mitral valve prosthesis 400 includes an outer support structure 404 and an inner support structure 412. In one aspect of the invention, inner support structure 412 includes at least two outer engagement arms 406 and at least two commissural sealing members 420. Each commissural sealing member 420 is positioned at approximately 90 degrees to each engagement arm 406. In alternative aspects of the invention, the commissural sealing members 420 can be positioned at angles greater than or less than 90 degrees to each engagement arm 406. As shown, the outer support structure includes diamond-shaped cells (or struts) 422. Alternative shapes and configurations of the cells can be employed. Inner support structure 412 further includes two anchor attachment points 424. Each anchor attachment point 424 is configured to attach to the heart via an anchor 414 to provide fixation support and to prevent migration of prosthesis 400 into the ventricle. Each anchor 414 further includes a tether 416 which provides further stability to the mitral valve prosthesis 400. A first end of each anchor 414 is attached to the anchor attachment points 424, while a second end of the anchor is attached to an anchoring element 418. In one aspect of the invention, anchoring element 418 is a hook. In alternative aspects of the invention, the anchoring element 418 can be a clip or a screw. The anchoring element 418 is configured to attach to the heart to provide further fixation support and to prevent migration of prosthesis 400 into the ventricle. In one aspect, anchoring element 418 is configured to attach to the wall of the left ventricle. In an alternative aspect, the anchor 414 is configured to be sutured to the heart. Like prosthesis 100, a prosthetic valve 408 can be attached to inner support structure 412 at specific positions 410. In one embodiment, the prosthetic valve is sewn onto inner support structure 412 as described in U.S. Patent Application Publication No. 2008/0071368, which is incorporated herein by reference in its entirety. The prosthetic valve can be formed of a biocompatible synthetic material, synthetic polymer, an autograft tissue, xenograft tissue, or other alternative materials.

In one aspect of the invention, anchor 414 is a suture comprised of a biocompatible material. In another aspect of the invention, anchor 414 is a wire comprised of a biocompatible material. In yet another aspect of the invention, anchor 414 is a chord comprised of a biocompatible material. In another aspect of the invention, anchor 414 is any biocompatible material. In one aspect, the biocompatible material is linearly elastic. In another aspect, the biocompatible material is viscoelastic. In yet another aspect, the biocompatible material can be engineered to have any desired property. In one embodiment, the biocompatible material can be a composite fiber of PTFE, elastane, and binder. In another embodiment, the biomaterial can also be an autograft, allograft, or xenograft used as a transplant material. In another embodiment, the biomaterial can be formed of a memory alloy such as NITINOL. In yet another embodiment, the biomaterial can be any biocompatible polymer or biocompatible metal known in the art. In one aspect, the elastic nature of the biocompatible material is optimized so it can provide a constant force and not elongate over time. In another aspect, the biocompatible material can be reinforced to have optimum fatigue performance. In one aspect of the invention, anchor 414 is configured to function as a tether. In yet another aspect, anchor 414 can be configured to function as an artificial *chordae*. In still another aspect, the anchor can be configured to function as an anchoring element.

Figure 4B:
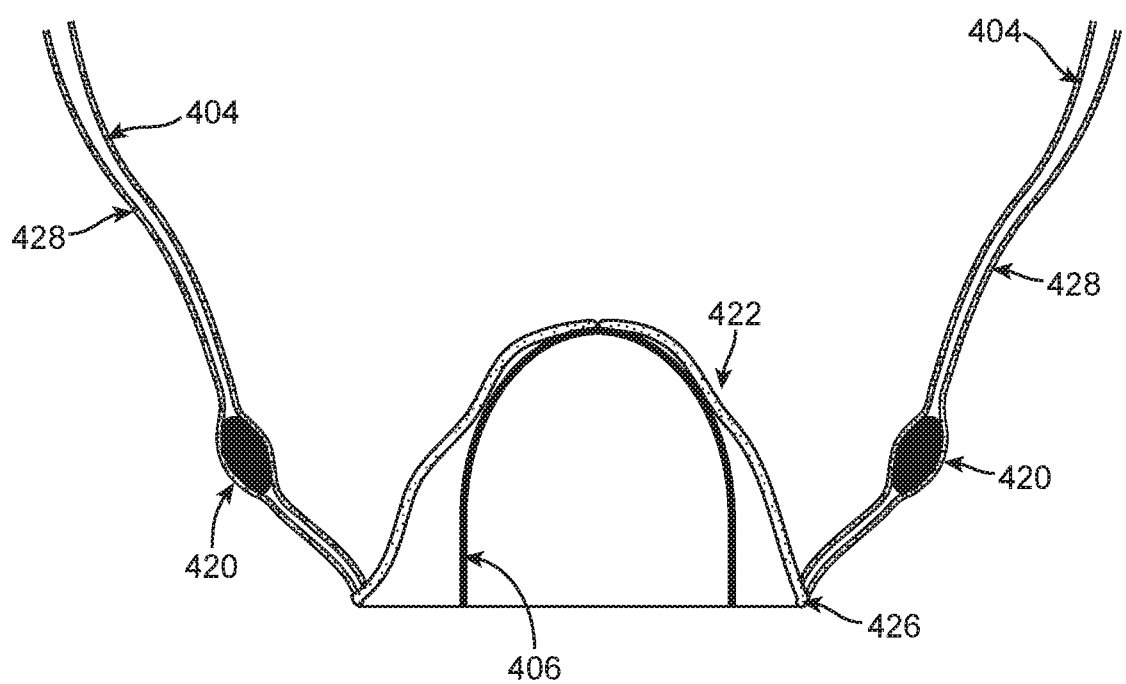
FIG. 4B is a perspective view of a mitral valve prosthesis, according to an aspect of this disclosure.

FIG. 4B is a perspective view of a mitral valve prosthesis 400 positioned at the mitral annulus 426 so that the engagement arm 406 is positioned to clamp the native valve leaflet 422. The commissural sealing members 420 are positioned at 90 degrees to the engagement arm 406 to provide an effective seal between the outer support structure 404 of the mitral valve prosthesis 400 and the walls of atrium 428, thereby sealing the native commissures of the heart and preventing peri-valvular leakage. In alternative aspects of the invention, the commissural sealing members 420 can be positioned at angles greater than or less than 90 degrees to the engagement arm 406. The frame seating relies on the engagement arms 406 pulling tension on the native *chordae tendinae* and the sandwich effect of the native valve leaflet 422 and the atrial tissue 424 being trapped by the engagement arm 406 and the outer support structure 404 of the mitral valve prosthesis 400.

Provided herein are also methods for treating mitral valve disorders in patients. In one embodiment, the method for treating mitral valve disorders in a patient's heart comprises a) inserting a delivery device into the left ventricle of the heart, b) advancing a mitral valve prosthesis via the delivery device into the left ventricle of the heart, c) advancing the delivery device into the native mitral valve such that the engagement arms seat on the outer surface of the native mitral valve leaflets, d) attaching the mitral valve prosthesis to the heart via at least one anchor, and e) adjusting tension on the anchor to prevent peri-valvular leakage. The mitral valve prosthesis comprises an expandable inflow region formed of a plurality of cells and is configured to expand within and support against the walls of the left atrium. The expandable inflow region has a cross-sectional diameter larger than the annulus of the native mitral valve. The mitral valve prosthesis also comprises an expandable outflow region formed of a plurality of cells and configured to expand within and support against the native mitral valve annulus, wherein the expandable outflow region includes two or more engagement arms, at least two anchor attachment points, and a prosthetic valve.

In one aspect of the invention, the method involves inserting the delivery device transfemorally into the left ventricle of the heart. In another embodiment, the method involves inserting the delivery device transseptally into the left ventricle of the heart. In yet another embodiment, the method involves inserting the delivery device transapically into the left ventricle of the heart.

In one aspect of the invention, at least one anchor attachment point of the mitral valve used in treating the mitral valve disorder is attached to a proximal end of at least one anchor prior to advancing a mitral valve prosthesis via the delivery device into the left ventricle of the heart. In one aspect, at least one anchor attachment point of the mitral valve used in treating the mitral valve disorder is attached to a proximal end of at least one anchor after the mitral valve prosthesis is positioned at the mitral annulus.

In one aspect, the distal end of at least one anchor attachment point of the mitral valve used in treating the mitral valve disorder is attached to the heart prior to advancing a mitral valve prosthesis via the delivery device into the left ventricle of the heart. In another aspect, the distal end of at least one anchor attachment point of the mitral valve used in treating the mitral valve disorder is attached to the heart only after the mitral valve prosthesis is positioned at the mitral annulus.

In another aspect, the distal end of the anchor is attached to the heart. In another aspect, the anchor is sutured to the heart. In one aspect, the anchor is attached to the heart via an anchoring element. In alternative aspects of the invention, the anchoring element can be a hook, a clip, or a screw. In one aspect, the anchoring element of the mitral valve used in the method of treating a mitral valve disorder can be configured to attach to a papillary muscle of the heart. In another embodiment, the anchoring element can be configured to attach to the wall of the left ventricle. In yet another embodiment, the anchor can be configured to function as an artificial *chordae*. In one aspect, the anchor comprises a biocompatible material.

In one aspect of the invention, the expandable outflow region of the mitral valve used in the method of treating a mitral valve disorder further comprises at least one commissural sealing member. In another aspect, the expandable outflow region comprises at least two commissural sealing members. In another aspect, the expandable outflow region further comprises two or more commissure posts, wherein ends of the engagement arms are each coupled to one of the commissure posts.

The foregoing description has been presented for purposes of illustration and enablement, and is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A method of treating a disorder of a native mitral valve in a heart, comprising:
    inserting a delivery device with a mitral valve prosthesis transapically into a left ventricle of the heart;
    advancing the delivery device into the left ventricle to position the mitral valve prosthesis within the native mitral valve, wherein the mitral valve prosthesis comprises a prosthetic valve and a frame having an expandable inflow region, with a cross-sectional diameter larger than an annulus of the native mitral valve, and an expandable outflow region;
    releasing the mitral valve prosthesis from the delivery device to permit the inflow region to expand into apposition with a wall of a left atrium of the heart, and to permit the outflow region to expand into apposition with the annulus of the native mitral valve;
    positioning at least one anchor between the outflow region of the mitral valve prosthesis and the heart to tether the mitral valve prosthesis to the heart; and
    adjusting tension on the at least one anchor to provide stability to the mitral valve prosthesis,
    wherein the at least one anchor includes an anchoring element at a first end thereof, the anchoring element being configured in an open state to permit adjustment of the tension on the at least one anchor and in a closed state to attach the at least one anchor to the heart by gripping and holding the heart.

2. The method of claim 1, wherein the anchoring element is configured to be secured to a wall of the left ventricle.

3. The method of claim 1, wherein a second end of the at least one anchor is attached to the outflow region of the mitral valve prosthesis.

4. The method of claim 1, wherein the at least one anchor is of a biocompatible material.

5. The method of claim 4, wherein the at least one anchor comprises a suture.

6. The method of claim 4, wherein the at least one anchor comprises a wire.

7. The method of claim 4, wherein the at least one anchor comprises a chord.

8. The method of claim 1, wherein the anchoring element includes a pair of jaws that are configured to include the open state and the closed state.

9. The method of claim 8, wherein the pair of jaws are configured to allow for adjusting the tension on the at least one anchor when the pair of jaws are in the open state.

10. A method of treating a disorder of a native mitral valve in a heart, comprising:
    attaching a first end of at least one anchor to a mitral valve prosthesis;
    loading the mitral valve prosthesis about a deployment element of a delivery device such that a second end of the at least one anchor extends through a distal tip of the deployment element and the delivery device to be accessible exteriorly to the patient;
    inserting the delivery device with the mitral valve prosthesis transapically into a left ventricle of the heart;
    advancing the delivery device into the left ventricle to position the mitral valve prosthesis within the native mitral valve, wherein the mitral valve prosthesis comprises a prosthetic valve and a frame with an expandable inflow region formed of a plurality of cells and configured to expand against a wall of a left atrium of the heart, wherein the expandable inflow region has a cross-sectional diameter larger than an annulus of the native mitral valve, and an expandable outflow region formed of a plurality of cells and configured to expand against the annulus of the native mitral valve, and wherein the frame also includes at least one engagement arm configured to secure at least one native mitral valve leaflet of the native mitral valve;
    releasing the mitral valve prosthesis from the delivery device to expand against the wall of the left atrium and the annulus of the native mitral valve, wherein the at least one engagement arm of the frame secures the at least one native mitral valve leaflet;

retracting the delivery device and the deployment element while the mitral valve prosthesis remains attached via the at least one anchor to the distal tip of the deployment element of the delivery device, wherein upon completion of the retraction the at least one anchor extends through an interior of the mitral valve prosthesis with the second end of the at least one anchor being accessible exteriorly to the patient;

disengaging the second end of the at least one anchor from the distal tip of the deployment element of the delivery device and attaching the second end of the at least one anchor to an anchoring element;

inserting an anchoring element delivery device with the anchoring element transapically through the interior of the mitral valve prosthesis into the left ventricle of the heart;

positioning the at least one anchor between the outflow region of the mitral valve prosthesis and the heart and attaching the anchoring element to the heart to tether the mitral valve prosthesis to the heart; and adjusting tension on the at least one anchor to stabilize the mitral valve prosthesis within the native mitral valve.

11. The method of claim 10, wherein the anchoring element is configured to be secured to a wall of the left ventricle.

12. The method of claim 10, wherein the at least one anchor is of a biocompatible material.

13. The method of claim 12, wherein the at least one anchor comprises a suture.

14. The method of claim 12, wherein the at least one anchor comprises a wire.

15. The method of claim 12, wherein the at least one anchor comprises a chord.

16. The method of claim 10, wherein the anchoring element is configured in an open state to permit adjustment of the tension on the at least one anchor and in a closed state to attach the at least one anchor to the heart by gripping and holding the heart.

17. The method of claim 16, wherein the anchoring element includes a pair of jaws that are configured to include the open state and the closed state.

18. The method of claim 17, wherein the pair of jaws are configured to allow for adjusting the tension on the at least one anchor when the pair of jaws are in the open state.

* * * * *